United States Patent
Robinson et al.

(10) Patent No.: US 9,364,537 B2
(45) Date of Patent: Jun. 14, 2016

(54) TRANSITION METAL PORPHYRIN COMPLEXES AND METHODS OF TREATMENT USING SAME

(71) Applicants: Jayne B. Robinson, Dayton, OH (US); Shawn Swavey, Springboro, OH (US)

(72) Inventors: Jayne B. Robinson, Dayton, OH (US); Shawn Swavey, Springboro, OH (US)

(73) Assignee: UNIVERSITY OF DAYTON, Dayton, OH (US)

( * ) Notice: Subject to any disclaimer, the term of this patent is extended or adjusted under 35 U.S.C. 154(b) by 0 days.

(21) Appl. No.: 14/466,662

(22) Filed: Aug. 22, 2014

(65) Prior Publication Data

US 2016/0051676 A1    Feb. 25, 2016

(51) Int. Cl.
*A01N 43/90* (2006.01)
*A61K 41/00* (2006.01)
*A61L 2/08* (2006.01)
*A61N 5/06* (2006.01)

(52) U.S. Cl.
CPC ............ *A61K 41/0071* (2013.01); *A01N 43/90* (2013.01); *A61L 2/088* (2013.01); *A61N 5/062* (2013.01); *A61N 2005/0659* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 5,281,616 A | 1/1994 | Dixon et al. | |
| 5,545,516 A | 8/1996 | Wagner | |
| 6,030,767 A | 2/2000 | Wagner et al. | |
| 6,448,239 B1 | 9/2002 | Groves et al. | |
| 6,730,666 B1 * | 5/2004 | Yayon | A61K 31/409 514/183 |
| 7,030,176 B2 | 4/2006 | Nohr et al. | |
| 8,551,456 B2 | 10/2013 | Robinson et al. | |
| 8,563,712 B2 | 10/2013 | Che et al. | |
| 2001/0046662 A1 | 11/2001 | Wagner et al. | |
| 2003/0004204 A1 | 1/2003 | Sakalosky | |
| 2005/0090428 A1 | 4/2005 | Compans et al. | |
| 2006/0040914 A1 | 2/2006 | Roncucci et al. | |
| 2008/0051736 A1 | 2/2008 | Rioux et al. | |
| 2012/0065181 A1 | 3/2012 | Warner et al. | |

OTHER PUBLICATIONS

Costa et al., 7(4) Photochemical & Photobiological Sciences 415-422 (2008) (CAS Abstract).*
Tremblay-Morin et al., 46(41) Tetrahedron Letts. 6999-7002 (2005) (CAS Abstract).*
Gomer et al., Photochem. Photobiol., vol. 40, pp. 435-439 (1984).
"A Study of Closed vs. Open Shell Transition Metal Porphyrin Complexes", UMass Boston, Chem. 371, Advanced Inorganic Chemistry Laboratory (date at least as of May 30, 2014).
Zhuang, et al. "An unsymmetrical porphyrin and its metal complexes: synthesis, spectroscopy, thermal analysis and liquid crystal properties", J. Serb. Chem. Soc., vol. 74 (10), pp. 1097-1104 (2009).
Oliveira, et al. "Porphyrin derivatives as photosensitizers for the inactivation of Bacillus cereus endospores", The Society for Applied Microbiology, Journal of Applied Microbiology, vol. 106, pp. 1986-1995 (2009).
Cunningham, et al. "Highly Efficient Visible-Light-Induced Photocleavage of DNA by a Ruthenium-Substituted Fluorinated Porphyrin", Eur J. Inorg. Chem. pp. 1521-1525 (2009).
PCT, International Search Report and Written Opinion, International Application No. PCT/US2015/045266, Feb. 18, 2016.

* cited by examiner

*Primary Examiner* — Timothy R Rozof
(74) *Attorney, Agent, or Firm* — Thompson Hine LLP (57) ABSTRACT

A porphyrin of general formula (I) having a transition metal (II) cation in its core and one or two mono-, di-, tri-, tetra- or penta-halophenyl groups and two or three pyridyl groups in the 5, 10, and/or 15 positions of the porphyrin ring contributing to a positive two or three charge neutralized by the presence of a respective number of anions. The porphyrin of the general formula (I) characterized by killing *pseudomonas* bacteria in the dark.

20 Claims, 6 Drawing Sheets

PHOTOCLEAVAGE STUDIES OF PLASMID DNA

A = the free-base porphyrin after about twenty (20) minutes
B = a Zn porphyrin after only two (2) minutes 50:1 base pairs to complex, light filtered to only light in the PDT window of FIG. 2

FIG. 3

PHOTOCLEAVAGE STUDY: PLASMID DNA WITH ZN PORPHYRIN IN THE ABSENCE OF $O_2$

10:1 base pairs to complex, light filtered with a 420 nm filter, samples taken at 10 minute intervals

TRANSITION METAL PORPHYRIN COMPLEXES AND METHODS OF TREATMENT USING SAME

TECHNICAL FIELD

The present application relates to transition metal porphyrin complexes, more particularly to a 5,10,15-tris(N-methyl-X-pyridyl)-20-(pentahalophenyl)porphyrin with a transition metal inserted in the porphyrin core.

BACKGROUND

The use of light activated drugs is a very attractive option for the development of therapeutic methodologies that minimize damage to normal tissue by allowing spatial and temporal control over toxicity. Light activated drugs have been used for blood sterilization. For example, U.S. Pat. No. 6,030,767 (Wagner et al.) describes photosterilizing blood and blood components, such as red blood cells or plasma, using methylene blue derivatives. See also, e.g., U.S. Pat. No. 5,545,516 (Wagner) and U.S. Pat. Publ. 2001/0046662 A1 (Wagner et al.). Photodynamic therapy (PDT) has also been used as a treatment for several forms of cancer. PDT works by exposing a photosensitizing drug to specific wavelengths of light in the presence of oxygen. When this reaction occurs, the normally innocuous photosensitizing drug becomes cytotoxic via an activated species of oxygen, known as singlet oxygen. Some of these phototoxic agents can be given orally and are preferentially retained by tumor cells. PDT has been used effectively for ovarian cancer, lung cancer, breast cancer, esophogeal cancer, skin cancers and bladder cancers. However, because the effects of almost all PDT drugs are oxygen dependent, photosensitization typically does not occur in anoxic areas of tissue. For example, in vivo studies showed that induction of tissue hypoxia, by clamping, abolished the PDT effects of porphyrins (Gomer et al., Photochem. Photobiol., 40:435-439 (1984)).

SUMMARY

In one aspect, a porphyrin of general formula (I) is disclosed. General formula (I) is wherein, M is a transition metal (II) cation, R is a mono-, di-, tri-, tetra-, or penta-halophenyl and the halogen is selected from the group consisting of Cl, F, Br, and combinations thereof, R' is R" is equal to R or R', R''' is —H, —F, —Cl, or —Br, and Y is 2 or 3.

In one embodiment, M is selected from the group consisting of $Fe^{+2}$, $CO^{+2}$, $Ni^{+2}$, and $Zn^{+2}$. In another embodiment, R" is equal to R' and M is $Zn^{+2}$, and further R' is N-methyl-4-pyridyl, R is pentfluorophenyl, and R''' is —H. The porphyrin may also include anions to neutralize the charges on the ring. In one embodiment, Y is 3 and the anions are each p-toluene sulfonate.

In another embodiment, M is $Zn^{+2}$, R" is equal to R and R is pentfluorophenyl, and further R' is N-methyl-4-pyridyl, Y is 2 and the anions are each p-toluene sulfonate.

In accordance with a particular aspect, compositions are disclosed that include at least one of the porphyrins described herein, as an active principle, in a therapeutically acceptable medium. In one embodiment, the composition is a sterilizing or cleansing composition that includes a therapeutically effective amount of the porphyrin(s) for sterilizing or cleaning an object or a surface.

In another embodiment, the composition includes a therapeutically effective amount of the porphyrin(s) to treat diseased cells. Here, the composition may be an inhalable composition having the porphyrin(s) present in an inhalable therapeutically acceptable medium.

In accordance with another aspect, a method for sterilizing or cleaning a surface is disclosed. The method includes contacting a surface with a therapeutically effective amount of one or more of the porphyrins described herein. The method may also include photoactivating the porphyrin with light comprising one or more wavelengths in the range of about 400 nm to about 850 nm. In one embodiment, the surface being treated may be a biofilm, a medical instrument, a filter, or a household surface.

In another aspect, a method for phototherapy is disclosed. The method includes administering one or more of the porphyrins described herein in a therapeutically effective amount to a source of a substance to be treated, and activating the porphyrin with light comprising one or more wavelengths in the range of about 400 to about 850 nm in the presence or absence of oxygen. In one embodiment, the source is a patient, the substance is diseased cells, and administering includes topically applying the porphyrin, orally inserting or ingesting the porphyrin, inhaling the porphyrin, or intravenously applying the porphyrin. In another embodiment, the source is a solution and the substance is DNA or RNA, and administering includes adding the porphyrin to the solution at a solution concentration of about 5 DNA or RNA base pairs per porphyrin to about 75 DNA or RNA base pairs per porphyrin to form a mixture thereof, and wherein the phototherapy photonicks the DNA or RNA.

DETAILED DESCRIPTION

The following detailed description will illustrate the general principles of the invention, examples of which are additionally illustrated in the accompanying drawings. In the drawings, like reference numbers indicate identical or functionally similar elements.

The porphyrins disclosed herein are water soluble and have a transition metal (II) cation inserted into the porphyrin core. The theory behind adding the transition metal (II) cations into the porphyrin core was to increase the excited state lifetime, which it does, but surprisingly the transition metal porphyrin complexes are also very good at killing bacteria in the dark (i.e., the absence of light). This ability to kill bacteria was a complete surprise, in particular the ability to kill *Staphylococcus aureus*.

The transition metal porphyrin complexes disclosed herein are also effective photosensitizers. The transition metal porphyrin complexes when compared to a commercially available photosensitizer, such as Photofrin, has several advantages: (1) it is easier to purify; (2) it need not be a mixture (the transition metal porphyrin is merely present in water); (3) it has a higher binding affinity toward DNA, (4) it is efficient at photoreactions with DNA at low energy; and (5) it is efficient at killing bacteria in the dark.

The transition metal porphyrins disclosed herein have the general formula (I) shown below.

wherein,

M is a transition metal (II) cation,

R is a mono-, di-, tri-, tetra-, or penta-halophenyl and the halogen is selected from the group consisting of Cl, F, Br, and combinations thereof, R' is

R'' is equal to R or R',

R''' is —H, —F, —Cl, or —Br, and

Y is 2 or 3.

The transition metal M is a $Fe^{+2}$, a $Co^{+2}$, a $Ni^{+2}$, or $Zn^{+2}$.

In one embodiment, R'' is equal to R' and M is $Zn^{+2}$. In this embodiment, R' may be N-methyl-4-pyridyl, R is pentfluorophenyl, R''' is —H and Y equals 3 and the anion is p-toluene sulfonate. This porphyrin is a meso-5,10,15-tris(N-methyl-4-pyridyl)-20-(pentafluorophenyl)porphyrinatozinc(II), tris-p-toluene sulfonate (ZnPFPTMP) and shown below.

In another embodiment, R'' is equal to R, R is pentfluorophenyl, and M is $Zn^{+2}$. In this embodiment, R' is N-methyl-4-pyridyl, R''' is —H, Y equals 2 and the anion is p-toluene sulfonate cations. This porphyrin is a meso-5,15-di(N-methyl-4-pyridyl)-10,20-di(pentafluorophenyl)porphyrinatozinc(II), di-p-toluene sulfonate and shown below.

Figure 5:
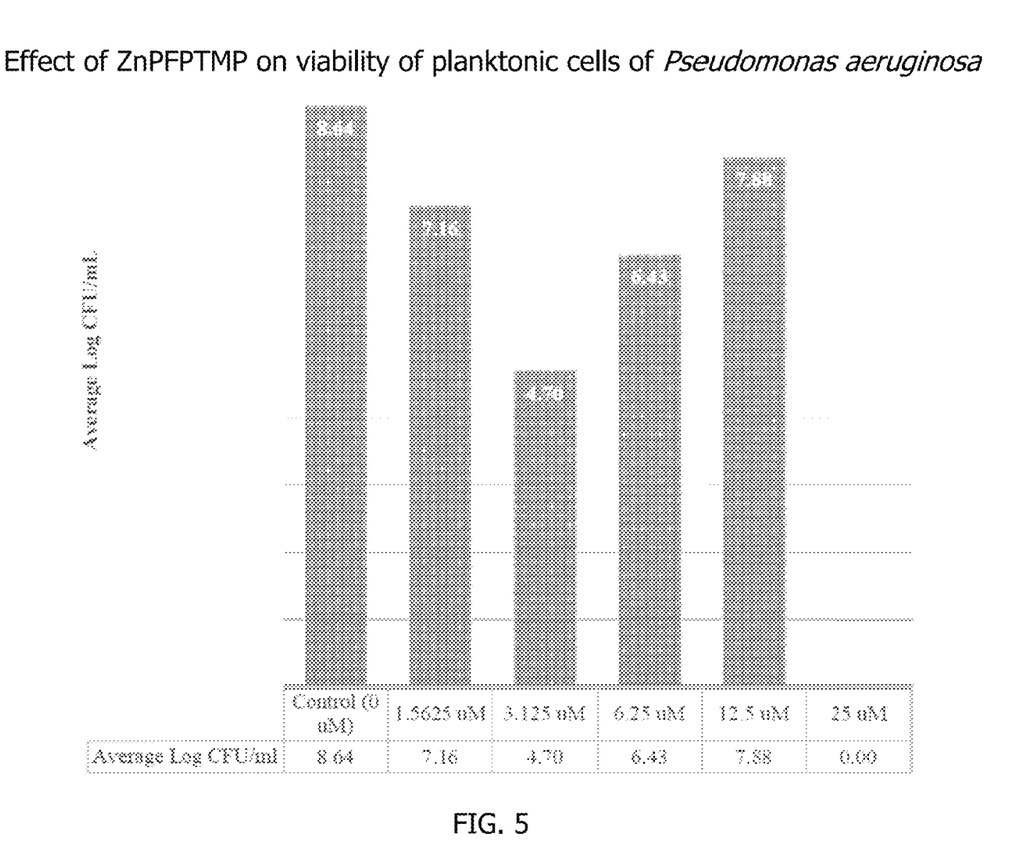
FIG. 5 is a graph of the effect of ZnPFPTMP on planktonic cells of *Pseudomonas aeruginosa* in the absence of light.

The porphyrins of general formula (I) are water soluble. Surprisingly and unexpectedly, the porphyrins of general formula (I) kill bacteria in the dark. The ability to kill bacteria in the dark was shown by treating *Pseudomonas aeruginosa* cells: planktonic and biofilm associated cells with ZnPFPTMP in the absence of light. ZnPFPTMP was added to cell suspensions at the concentrations shown in FIG. 5 (0 to 100 µM) and incubated at 37° C. in the absence of light. At the end of seven (7) hours viability was determined by plating cell suspensions onto Luria broth (LB) agar plates and determining the viable plate counts (CFU/ml). The MLC (minimum lethal concentration) was determined to be 25 uM, where there were no survivors. There was substantial killing at two (2) hours as well. Biofilms were prevented when the ZnPFPTMP was added to cell suspensions incubated in the dark, presumably due to the toxicity to planktonic cells. When preformed biofilms were exposed to the ZnPFPTMP in the dark there was a 2.7 log reduction in the presence of the *Pseudomonas aeruginosa* (data not shown).

Figure 6:
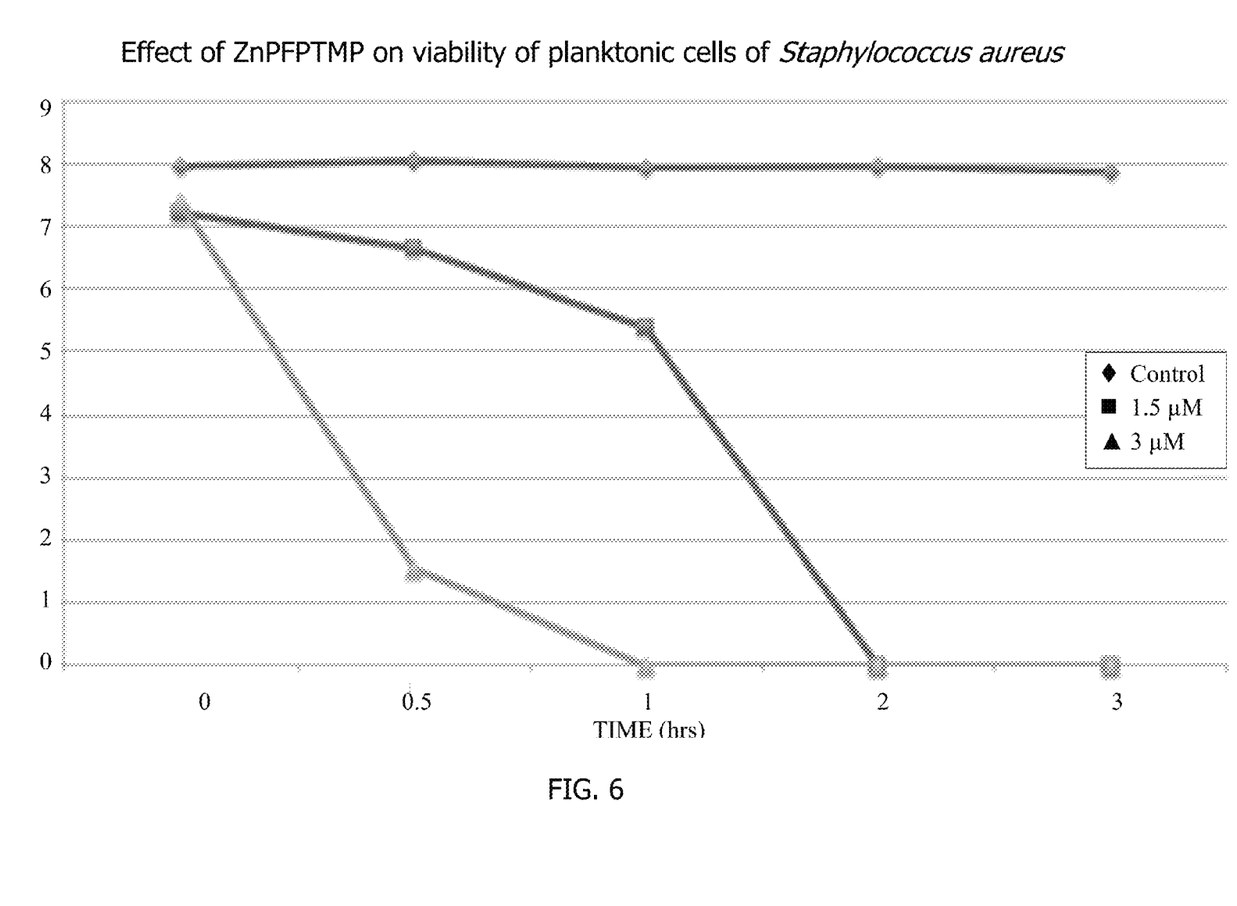
FIG. 6 is a graph of the effect of ZnPFPTMP on planktonic cells of *Staphylococcus aureus* in the absence of light.

Additionally, the ability of ZnPFPTMP to affect killing of bacteria in the absence of light was further tested against the Gram-positive pathogenic bacterium *Staphylococcus aureus*. This bacterium was chose to evidence the ability of the porphyrins of general formula (I) to treat/kill methicillin-resistant *Staphylococcus aureus* (MRSA) without exposing the scientists to MRSA directly. Moreover, it is believed that the mechanism used by the porphyrins of general formula (I) is unlikely to involve the methicillin resistance mechanism. *S. aureus* cells grown in LB medium were washed and re-suspended on 0.2% peptone and exposed to either 1.5 µM or 3.0 µM Zeke in sterile water. Cell suspensions were sampled every 30 minutes for 3 hours and plated to determine viability. The results of these tests are shown in the graph provided in FIG. 6. After 30 min in the presence of 3.0 µM Zeke there was a 5.5 log reduction in viable cells of *S. aureus*, and after 60 min no viable cells remained. At 1.5 µM Zeke's complete elimination of viable cells of *S. aureus* took only two hours.

EXAMPLE 1

Using ZnPFPTMP as an example porphyrin, one method of its synthesis is provided below.

Part A: Synthesis of meso-5,10,15-tris(4-pyridyl)-20-(pentafluorophenyl)porphyrin A solution containing 4.3 mL of 4-pyridine carboxaldehyde and 1.9 mL of pentafluoro benzaldehyde in 100 mL of propionic acid was first heated for 10 minutes. To this solution was added 4.2 mL of freshly distilled pyrrole and the reaction mixture was heated to reflux for 2 hours. The reaction mixture was allowed to cool to room temperature. Then, the mixture was divided into two fractions (50 mL each) and each fraction was neutralized with ice cooled (50:50) methanol: ammonia. The slurry was filtered by vacuum filtration and the powder was air dried. The powder was dissolved in methylene chloride and chromatographed on silica gel using an ethanol: ethylacetate (50:50) mixture as eluent. Three bands were separated on the column. The third band off the column was collected yielding 120 mg (15 mmoles, 1.11% yield). Analysis by UV/Vis ($CH_3CN$) $\lambda_{max}$ (nm) [$\epsilon \times 10^{-4}$ $M^{-1}$ $cm^{-1}$], $^1H$ NMR (300 MHz, $CDCl_3$, TMS), and calculations for the formula $C_{41}H_{22}N_7F_5 \cdot 1H_2O$, confirmed that the product collected in the third band is a meso-5,10,15-tris(4-pyridyl)-20-(pentafluorophenyl)porphyrin Part B: Synthesis of meso-5,10,15-tris(N-methyl-4-pyridyl)-20-(pentafluorophenyl)porphyrin, tris-p-toluene sulfonate To methylate the product from Part a, meso-5,10,15-tris(4-pyridyl)-20-(pentafluorophenyl)porphyrin, to a solution containing 100 mg of the product of Part A in 20 mL of dichloromethane was added a large excess of methyl p-toluenesulfonate. The solution was refluxed until a precipitate formed (approximately 4 hours). The precipitate was filtered, washed with dichloromethane, and air dried to give between 60-80% yield. UV/vis (water) gave a Soret band at 419 nm with a molar absorptivity of $1.7 \times 10^5$ $M^{-1}$ $cm^{-1}$ and four less intense Q-bands between 500 and 650 nm.

Part C: synthesis of meso-5,10,15-tris(N-methyl-4-pyridyl)-20-(pentafluorophenyl)porphyrinatozinc(II), tris-p-toluene sulfonate In 5 mL of dimethylformamide (DMF) 200 mg of meso-5,10,15-tris(N-methyl-4-pyridyl)-20-(pentafluorophenyl)porphyrin, tris-p-toluene sulfonate from Part B was added a slight excess (1.5 equivalents) 58 mg of $ZnCl_2$ hexahydrate. The solution was refluxed for 30 minutes and added to 200 mL of dichloromethane. The precipitate was filtered, washed with dichloromethane, and air dried to give a yield of approximately 90%. UV/vis (water) gave the characteristic red shifted Soret band at 431 nm (molar absorptivity of $6.4 \times 10^5$ $M^{-1}$ $cm^{-1}$) and two Q-bands from 550-650 nm, indicative of insertion of zinc into the porphyrin core.

Figure 1:
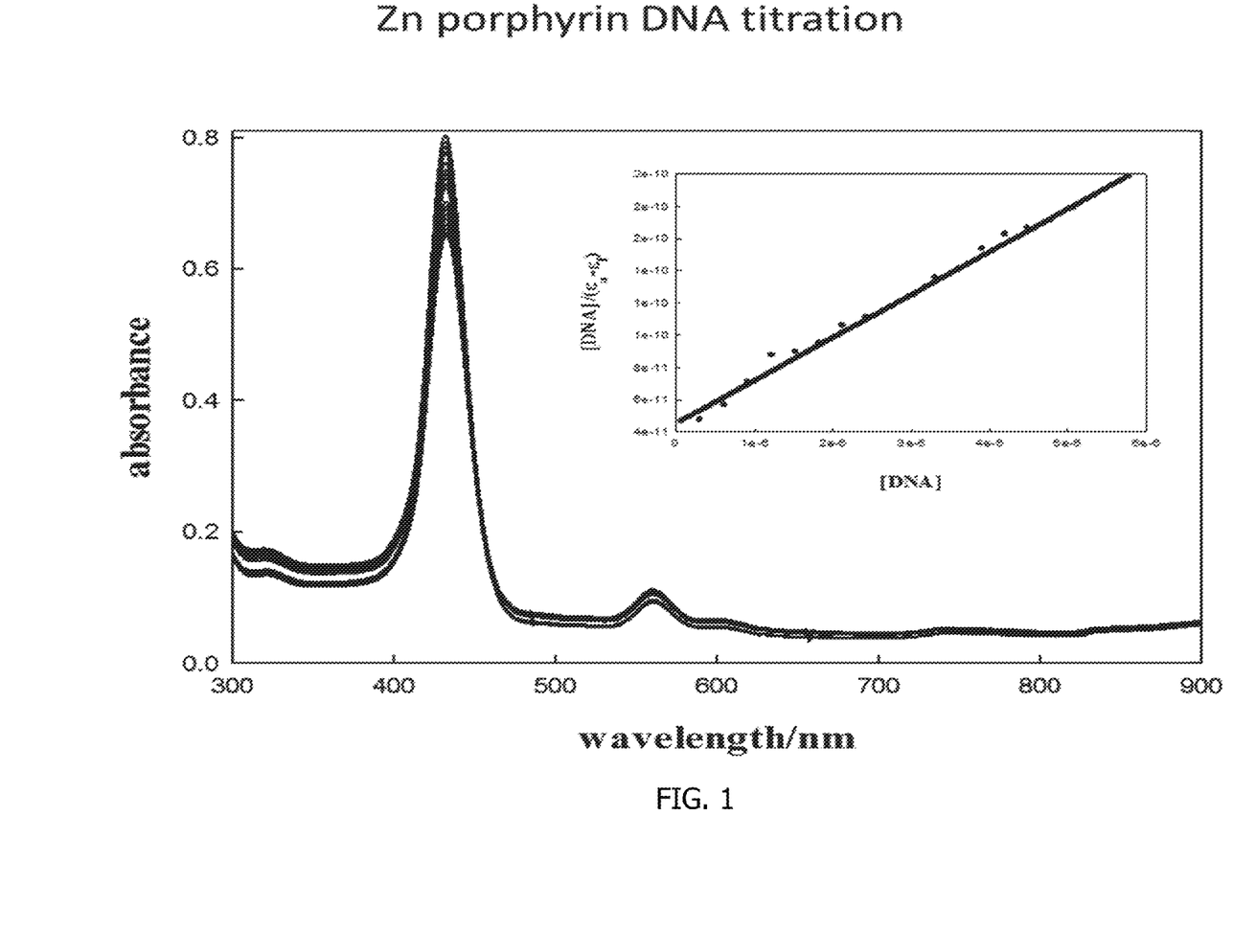
FIG. 1 is a graph of a Zn porphyrin DNA titration of meso-5,10,15-tris(N-methyl-4-pyridyl)-20-(pentafluorophenyl)porphyrinatozinc(II), tris-p-toluene sulfonate (referred to herein as ZnPFPTMP).

A sample of ZnPFPTMP from Part C was tested by various methods and techniques to determine how this compound may be utilized. In one test ZnPFPTMP was titrated into a DNA sample to determine ZnPFPTMP's affinity for binding to DNA. This test was conducted by measuring the absorption spectra of pH 7.2 buffer solutions (ionic strength=0.1 M) of ZnPFPTMP in the presence of increasing amounts of calf thymus CT-DNA. A graph of the titration is presented in FIG. 1. The graph shows binding constants of greater than $10^6$, which is very high, thereby suggesting intercalation of ZnPFPTMP into the DNA ladder.

Figure 2:
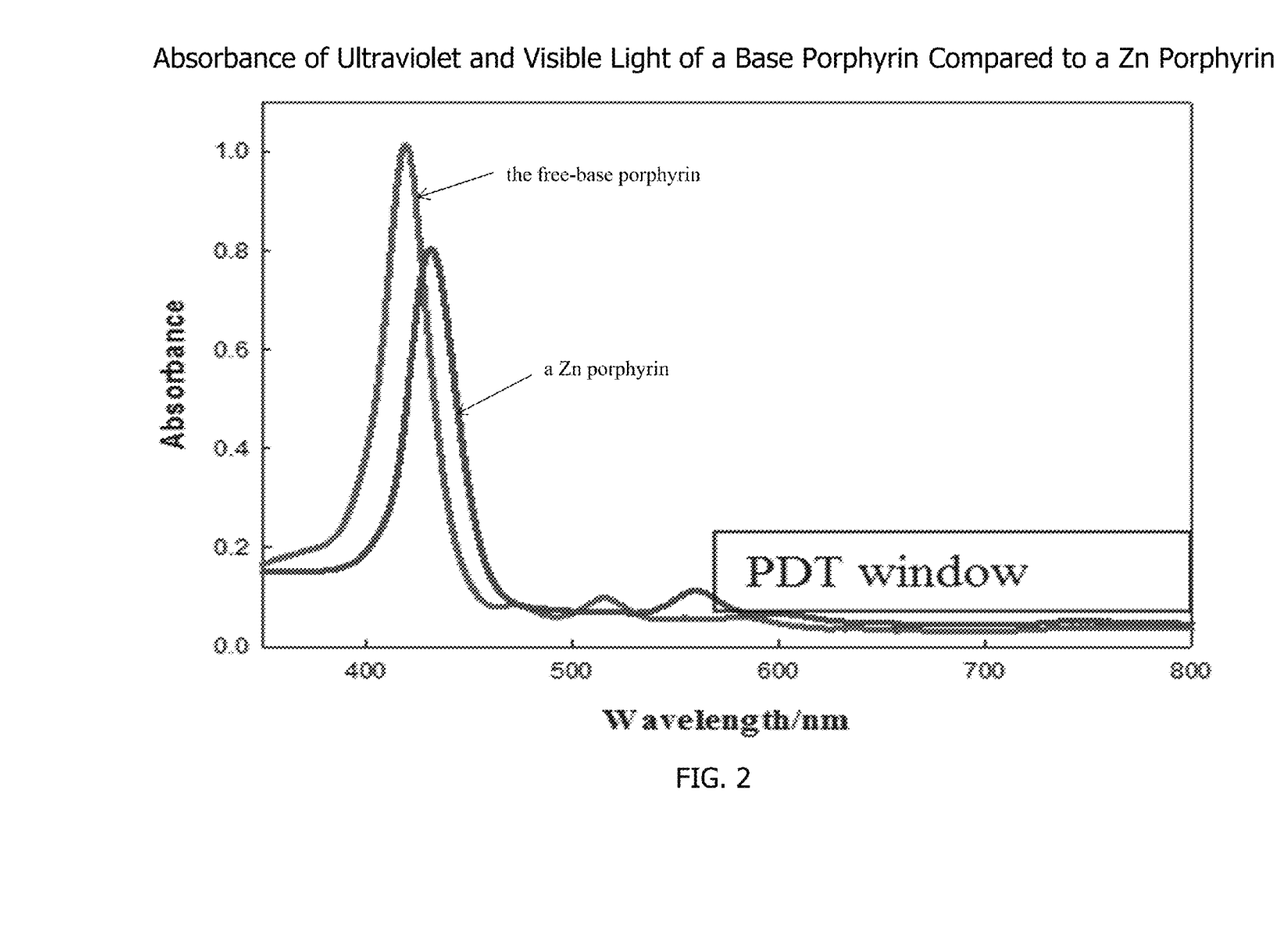
FIG. 2 is a graph of absorbance versus wavelength comparing the free-base porphyrin (no Zn present) and ZnPFPTMP.

Now referring to FIG. 2, ZnPFPTMP was compared to its free-base porphyrin (i.e., no zinc in the porphyrin core) in the ultraviolet (UV) and visible wavelength ranges for absorbance. As seen in FIG. 2, ZnPFPTMP has a right shift in its absorbance profile compared to the free-base porphyrin and more importantly has more absorption within the photodynamic therapy (PDT) window between about 575 nm to about 800 nm than the free-base porphyrin.

Photodynamic therapy (PDT) involves the use of photochemical reactions mediated through the interaction of photosensitizing agents (here the transition metal porphyrin complexes), light, and oxygen for the treatment of malignant or benign diseases. Photodynamic therapy is generally a 2-step procedure. In the first step, the photosensitizer is administered to the patient (human or animal) or to tissue or cells by one of several routes including, but not limited to, topical, oral, and intravenous administration and is allowed to be taken up by the target cells. The second step involves the activation of the photosensitizer in the presence of oxygen with a specific wavelength of light directed toward the target tissue. Because the photosensitizer is preferentially absorbed by a preselected, targeted area to be treated and the light source is directly targeted on that area to be treated, photodynamic therapy achieves dual selectivity, minimizing damage to adjacent healthy structures. The light used in photodynamic therapy may have a wavelength of about 500 nm to about 850 nm.

Figure 3:
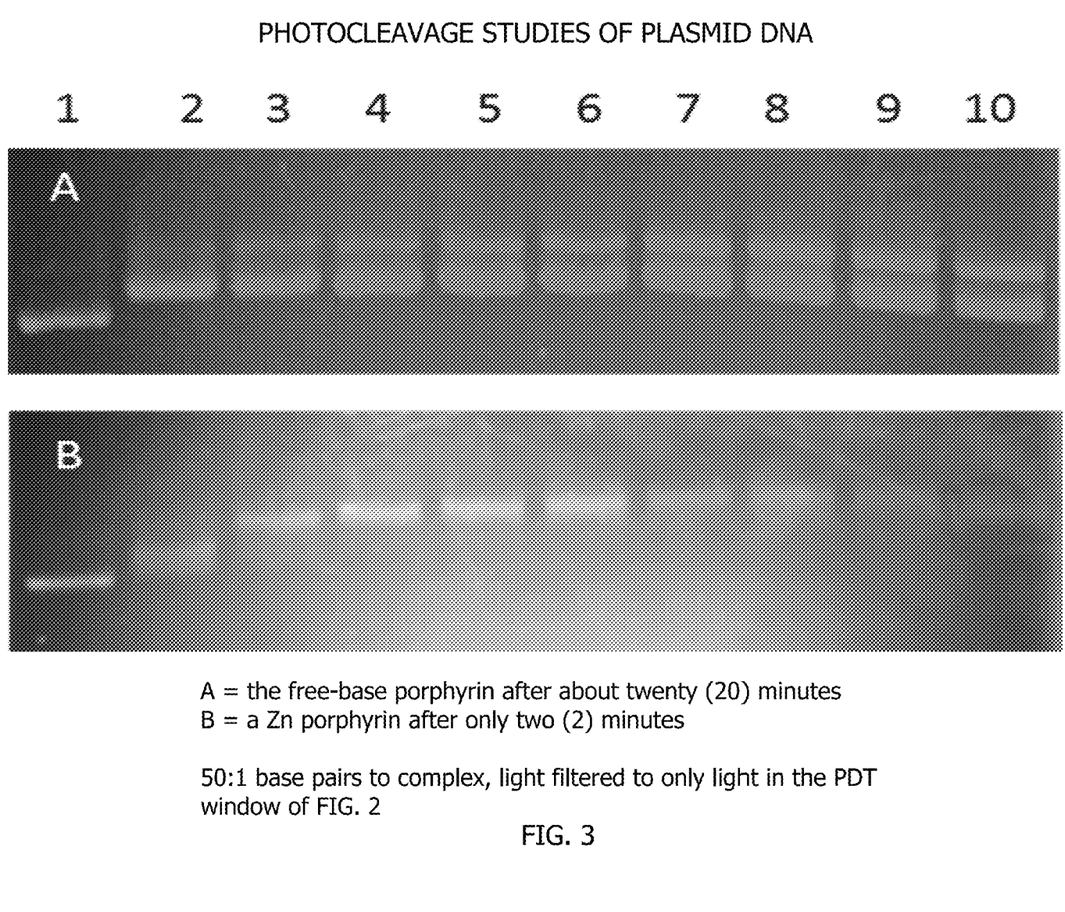
FIG. 3 displays the results of photocleavage studies of plasmid DNA by A, the free-base porphyrin after twenty minutes to wavelengths in the PDT window of FIG. 2. and by B, ZnPFPTMP after only two minutes under the same conditions.

To appreciate the significance of the increased absorption of ZnPFPTMP in the PDT window, comparative photocleavage studies of plasmid DNA under normal conditions (i.e., in the presence of oxygen) were conducted for ZnPFPTMP and its free-base porphyrin. As seen in FIG. 3, (B) ZnPFPTMP has more intense bands after only two (2) minutes compared to (A) its free-base porphyrin after twenty (20) minutes. In FIG. 3, gel electrophoresis of circular plasmid DNA (pUC18) in the absence (lane 1) and presence (lanes 2-10) of unmetallated porphyrin (A) and ZnPFPTMP (B) at a 50:1 base pair to complex ratio are shown. Samples were irradiated with a 300 W mercury arc lamp equipped with a long pass filter, cutting off wavelengths below 550 nm, and were taken at 2 minute intervals.

The results with ZnPFPTMP after only two minutes reveals effective compete photonicking of the plasmid DNA, which was surprisingly effective in a very short time. ZnPFPTMP is very reactive at such low energy wavelengths of light.

Figure 4:
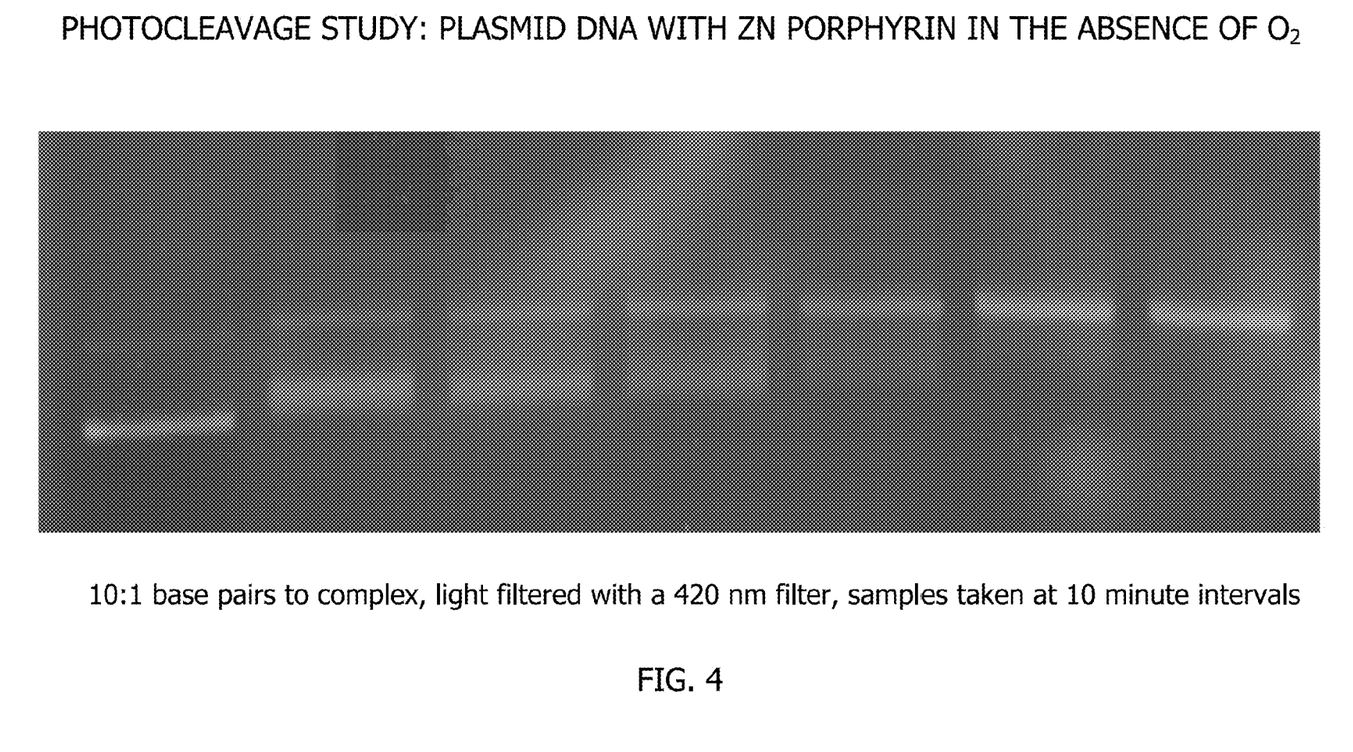
FIG. 4 displays the results of a photocleavage study of plasmid DNA by ZnPFPTMP in the absence of oxygen.

Even more surprising, ZnPFPTMP was even effective at photonicking DNA in the absence of oxygen. Referring now to FIG. 4, photocleavage studies based on a 10 to 1 base pairs to ZnPFPTMP was irradiated with a 420 nm filter and samples were taken at 10 minute intervals. In FIG. 3, gel electrophoresis of circular plasmid DNA (pUC18) in the absence (lane 1) and presence (lanes 2-10) of ZnPFPTMP at a 10:1 base pair to complex ratio is shown. Samples were irradiated with a 300 W mercury arc lamp equipped with a long pass filter, cutting off wavelengths below 420 nm in the absence of oxygen, and were taken at 10 minute intervals. Accordingly, ZnPFPTMP can be effective under hypoxic conditions.

ZnPFPTMP through the synergistic effect of the presence of a transition metal in the core and a pentafluoro and methylated pyridyl groups provides significant and unexpected improvements in photodynamic therapy. Porphyrins of general formula (I), including ZnPFPTMP, will be able to reduce treatment time necessary in photodynamic therapy and/or the use of lower concentrations (lower dosing) of the porphyrin since it is so effective. A reduction in treatment times means less possibility of potential toxicity exposure for patients and decreases the possibility of potential damage to surrounding healthy tissue/cells.

In another aspect, compositions that include one or more of the porphyrins of general formula (I), as an active agent, in a therapeutically or pharmaceutically effective medium or carrier are disclosed. A "pharmaceutically effective medium or carrier" means a medium or carrier that is useful for the preparation of a pharmaceutical composition, i.e., generally compatible with the other ingredients of the composition. The formulations can conveniently be presented in unit dosage form and can be prepared by any methods known in the art of pharmacy. The amount of the porphyrin(s) combined with the carrier to produce a single dosage form will vary depending upon the subject being treated and the particular mode of administration. The amount of active ingredient which can be combined with a carrier material to produce a single dosage form will generally be the amount of the porphyrin(s) which produces a therapeutic effect. A therapeutically effective amount of a porphyrin of general formula (I) includes about 0.1 wt % to about 99.5 wt % of the composition. In another embodiment, the therapeutically effective amount, may be about 0.5 wt % to about 90 wt %.

When the composition is an orally administrable composition, the medium may be an aqueous medium. The aqueous medium includes one or more of purified water and ethanol, and is preferably purified water. The orally administrable composition may further comprise one or more pharmaceutically effective excipient such as antioxidants, sweetening agents, preservatives, viscosity modifying agents and a mixture thereof.

The antioxidant may be sodium pyrosulfite, ascorbic acid, erythorbic acid and a mixture thereof, but is not limited thereto. The amount of the antioxidant is employed in an amount of 0.1 to 100 mg, preferably 1 to 10 mg per 100 mL of the composition.

The sweetening agent may be white sugar, potassium acesulfame, saccharine, dextrose and a mixture thereof, but is not limited thereto. The amount of the sweetening agent is employed in an amount of 5 to 100,000 mg, preferably 10 to 50,000 mg per 100 mL of the composition.

The preservative may be methyl paraoxybenzoic acid, ethyl paraoxybenzoic acid, isopropyl paraoxybenzoic acid, sorbic acid, potassium sorbate, sodium sorbate and a mixture thereof, but is not limited thereto. The amount of the preservative is employed in an amount of 5 to 200 mg, preferably 10 to 100 mg per 100 mL of the composition.

The viscosity modifying agent may be glycerin, polyvinylpyrrolidone, ethyl cellulose, sodium carboxymethylcellulose and a mixture thereof, but is not limited thereto. The amount of the viscosity modifying agent is employed in an amount of 100 to 20,000 mg, preferably 200 to 10,000 mg per 100 mL of the composition.

When the composition is a topical composition, the therapeutically acceptable medium includes one or more of water, glycerol, ethanol, propanediol, butylene glycol, dipropylene glycol, ethoxylated or propoxylated diglycols, cyclic polyols.

Preferably, the compositions according to the invention are in a form suitable for topical application including a cosmetically effective medium. By "cosmetically effective", we mean media that are suitable for use in contact with human skin or skin appendages, without risk of toxicity, incompatibility, instability, allergic response or the like. The compositions intended to be applied to the skin can be in the form of a cream, an oil-in-water emulsion, or a water-in-oil or multiple emulsion, a solution, a suspension, a microemulsion, an aqueous or anhydrous gel, a serum or a vesicle dispersion, a patch, a spray, an ointment, a pomade, a lotion, a colloid, a milk, a lotion, a stick or a powder, all suitable for application on the skin, lips and/or skin appendages.

In addition to the porphyrin of general formula (I), the topical composition may include additives (adjuvants) such as solvents, diluents, dyes, sunscreens, self-tanning agents, pigments, fillers, preservatives, odor absorbents, thickening agents, emulsifiers, moistening agents, emollients, fragrances, antioxidants, film-forming agents, chelating agents, sequestering agents and conditioners can be added to the composition. In every case, a person skilled in the art will make sure that these adjuvants as well as the proportions thereof are chosen so as not to adversely affect the desired advantageous properties of the composition according to the invention. These adjuvants can be, for example, between 0.01 and 20% of the total weight of the composition ("wt %"). When the composition of the invention is an emulsion, the fatty phase can be 5 to 80 wt %, and preferably 5 to 50 wt %. The emulsifiers and co-emulsifiers used in the composition will be chosen among those classically used in the field considered. For example, they may be used in a proportion ranging from 0.3 to 30 wt %.

When the composition is intended for intravenous administration, the transition metal porphyrin complex may be dissolved in water as a pharmaceutically effective carrier. The pharmaceutically effective carrier may also include an isotonicity agent, a buffering agent, a pH modulator, and/or an antioxidant.

When the composition is intended to be inhaled into the lungs, a therapeutically effective amount of a porphyrin of general formula (I) includes about 0.1 to 50 mg/day. In one embodiment, the therapeutically effective amount is from 0.1 to 5 mg/day. In another embodiment, the therapeutically effective amount is from 0.4 to 1.6 mg/day. These dosage amounts may be administered from a metered delivery system in a series of from 1 to 5 puffs at each administration, with administration performed once to four times daily.

In one embodiment, the inhaler composition may include one or more of the transition metal porphyrin complexes in a pharmaceutically-effective semi-aqueous solvent comprising water and a glycol, in relative volume amounts sufficient (i) to aerosolize the composition to a mean mass medium aerodynamic diameter in the range of about 1 up to about 10 microns;

6. The porphyrin of claim 1, wherein M is $Zn^{+2}$, R'' is equal to R and R is pentfluorophenyl.

7. The porphyrin of claim 6, wherein R' is N-methyl-4-pyridyl, Y is 2 and each anion is p-toluene sulfonate.

8. The porphyrin of claim 1, wherein the porphyrin kills bacteria in an absence of light.

9. The porphyrin of claim 8, wherein the bacteria comprises *Staphylococcus aureus* or *Pseudomonas aeruginosa*.

10. A composition comprising:
    the porphyrin of claim 1, as an active principle, in a therapeutically acceptable medium.

11. The composition of claim 10, containing a therapeutically effective amount of the porphyrin for sterilizing or cleaning a surface.

12. The composition of claim 10, containing a therapeutically effective amount of the porphyrin to treat diseased cells.

13. The composition of claim 10, wherein the therapeutically acceptable medium is inhalable.

14. A method for sterilizing or cleaning a surface, the method comprising: contacting the surface with a therapeutically effective amount of the porphyrin of claim 1.

15. The method of claim 14, further comprising photoactivating the porphyrin with light comprising one or more wavelengths in the range of about 400 nm to about 850 nm.

16. The method of claim 14, wherein the surface is a biofilm, a medical instrument, a filter, or a household surface.

17. A method for phototherapy, the method comprising:
    administering the porphyrin of claim 1 in a therapeutically effective amount to a source of a substance to be treated; and
    activating the porphyrin with light comprising one or more wavelengths in the range of about 400 to about 850 nm in the presence or absence of oxygen.

18. The method of claim 17, wherein the source is a patient, the substance is diseased cells, and administering includes topically applying the porphyrin, orally inserting or ingesting the porphyrin, inhaling the porphyrin, or intravenously applying the porphyrin.

19. The method of claim 17, wherein the source is a solution and the substance is DNA or RNA, and administering includes adding the porphyrin to the solution at a solution concentration of about 5 DNA or RNA base pairs per porphyrin to about 75 DNA or RNA base pairs per porphyrin to form a mixture thereof, and wherein the phototherapy photonicks the DNA or RNA.

20. A porphyrin having the following structure:

* * * * *